(12) United States Patent
Ito et al.

(10) Patent No.: US 8,283,501 B2
(45) Date of Patent: Oct. 9, 2012

(54) OPTICALLY ACTIVE 2,2'-BIPHENOL DERIVATIVE AND PRODUCTION METHOD OF SAME

(75) Inventors: Yoshikazu Ito, Naka-gun (JP); Yasushi Kubota, Odawara (JP); Tsutomu Inoue, Chigasaki (JP)

(73) Assignee: Nippon Soda Co., Ltd., Tokyo (JP)

( * ) Notice: Subject to any disclaimer, the term of this patent is extended or adjusted under 35 U.S.C. 154(b) by 260 days.

(21) Appl. No.: 12/811,805
(22) PCT Filed: Jan. 6, 2009
(86) PCT No.: PCT/JP2009/000012
§ 371 (c)(1),
(2), (4) Date: Jul. 6, 2010
(87) PCT Pub. No.: WO2009/087959
PCT Pub. Date: Jul. 16, 2009

(65) Prior Publication Data
US 2010/0280284 A1 Nov. 4, 2010

(30) Foreign Application Priority Data
Jan. 8, 2008 (JP) .................... 2008-001275

(51) Int. Cl.
*C07C 39/15* (2006.01)
*C07C 37/68* (2006.01)
*C07C 37/86* (2006.01)

(52) U.S. Cl. ........ 568/730; 568/749; 568/750; 568/755; 568/756

(58) Field of Classification Search .................. None
See application file for complete search history.

(56) References Cited

U.S. PATENT DOCUMENTS
6,489,517 B1 * 12/2002 Shapiro .................... 568/730
(Continued)

FOREIGN PATENT DOCUMENTS
JP 10-45648 2/1998
(Continued)

OTHER PUBLICATIONS
Japanese Patent Office, International Search Report (translated) mailed Mar. 24, 2009, from related International Patent Application No. PCT/JP2009/000012.
(Continued)

*Primary Examiner* — Brian J Davis
(74) *Attorney, Agent, or Firm* — Kenyon & Kenyon LLP

(57) ABSTRACT

Disclosed herein are optically active biphenol derivatives represented by the following formulas (1) and (2), a method for optically resolving a biphenol derivative represented by formula (2'), a production method of an optically active biphenol derivative (1) comprising a step for reacting a Brønsted acid with a biphenol derivative (2), and a production method of an optically active biphenol derivative (3) comprising a step for reacting a Lewis acid with an optically active biphenol derivative (1) or an optically active biphenol derivative (2).

[CHEMICAL 1]

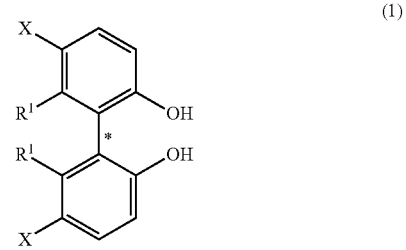

(1)

(2)

[CHEMICAL 2]

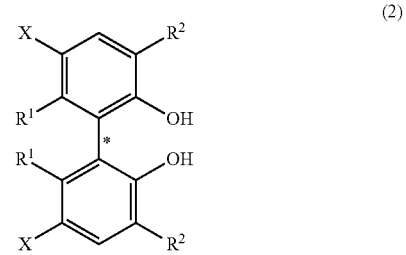

(2*)

[CHEMICAL 3]

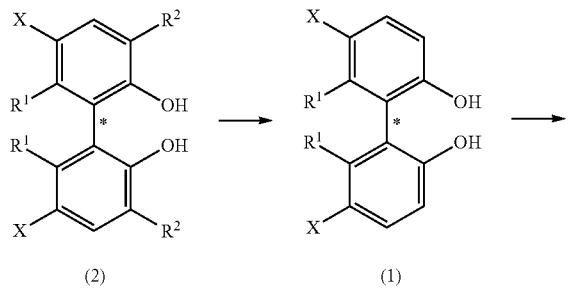

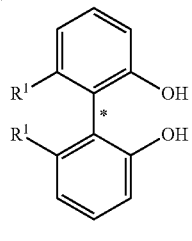

(3)

12 Claims, No Drawings

U.S. PATENT DOCUMENTS 6,555,718 B1 * 4/2003 Shapiro ............ 568/730
2004/0049087 A1 3/2004 Shapiro

FOREIGN PATENT DOCUMENTS

JP 2002-69022 3/2002
JP 2004-189696 7/2004

OTHER PUBLICATIONS

Harada et al., "Asymmetric Synthesis of 6,6'-Dialkyl and—Diphenyl-2,2'-Biphenyldiols by Using Menthone as a Chiral Template," *SYNLETT*, 1995, No. 3, pp. 283-284.

Kanoh et al., "Optical Resolution and Absolute Configuration of Axially Dissymmetric 2,2'-Dihydroxy-6,6'—dimethylbiphenyl," *Bull. Chem. Soc. Jpn.*, vol. 60, 1987, pp. 2307-2309.

H. E. Albert, "Reactions of 3,4,6-Trialkylphenols. III. Oxidation Studies," *J. Am. Chem. Soc.*, vol. 76, No. 19, 1954, pp. 4983-4985.

Yong-Gang Wang et al., "Design of Chiral Phase Transfer Catalyst with Conformationally Fixed Biphenyl Core: Application to Asymmetric Alkylation of Glycine Derivatives," *Organic Process Research & Development*, vol. 11, No. 3, pp. 628-632, 2007.

* cited by examiner

OPTICALLY ACTIVE 2,2'-BIPHENOL DERIVATIVE AND PRODUCTION METHOD OF SAME

This application is a national phase application of PCT/JP2009/000012 filed on Jan. 6, 2009 which claims priority under 35 U.S.C. 119 to Japanese Patent Application No. 2008-001275, filed on Jan. 8, 2008.

TECHNICAL FIELD

The present invention relates to an optically active 2,2'-biphenol derivative and a production method thereof, and more particularly, to an optically active 2,2'-biphenyl derivative, which is highly valuable for use in fields relating to the production of pharmaceutical and agrichemical bulk drugs and their production intermediates, and a production method thereof.

The present application claims priority on Japanese Patent Application No. 2008-001275, filed in Japan on Jan. 8, 2008, the content of which is incorporated herein by reference.

BACKGROUND ART

Optically active 2,2'-biphenol derivatives are important compounds as synthetic intermediates of ligands for asymmetric synthesis of various fine chemicals consisting primarily of pharmaceuticals and agrichemicals.

A known example of such a 2,2'-biphenol derivative is a 6,6'-disubstituted-2,2'-biphenol derivative represented by the following formula (A)

[CHEMICAL 1]

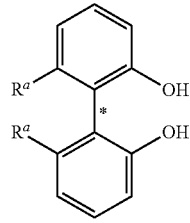

(A)

(wherein, $R^a$ represents an optionally substituted lower alkyl group, and * represents an axially asymmetric center).

Known examples of methods for obtaining an optically active 2,2'-biphenol derivative represented by the aforementioned formula (A) include a method in which a meso form of biphenyl is converted to an optically active compound followed by deriving to optically active 2,2'-biphenol, and a method in which a racemic form of 2,2'-biphenol is converted to a diastereomeric mixture followed by optical resolution.

Methods for producing meso and racemic forms of biphenols typically use oxidative ortho-coupling of a substituted resorcinol or substituted phenol by potassium hexacyanoferrate(III)(potassium ferricyanide), di-t-butyl peroxide, ferric chloride or oxygen and the like.

As an example of a method for converting a meso form of biphenyl to an optically active compound followed by deriving to optically active 2,2'-biphenol, a method is reported in Non-Patent Document 1 in which 2,2',6,6'-tetrahydrobiphenyl is converted to an acetal derivative of optically active menthone followed by deriving to an optically active 6,6'-disubstituted-2,2'-biphenol.

Examples of methods for converting a racemic form of 2,2'-biphenol to a diastereomeric mixture followed by optical resolution include a method in which a phosphoric acid derivative of a racemic form of 6,6'-disubstituted-2,2'-biphenol is esterified by reacting with optically active menthol followed by optical resolution (Patent Document 1), and a method in which only one of the optical isomers of a racemic form of 6,6'-disubstituted-2,2'-biphenol is selectively crystallized with optically active cyclohexanediamine (Patent Document 2).

However, the methods described in Non-Patent Document 1 and Patent Document 1 have a complex procedure due to the need for a multistage synthesis route, while the method of Patent Document 2 has the problem of low reaction yield.

In addition, although a method is known for synthesizing a racemic form of 3,3',6,6'-tetraalkyl-5,5'-dihalogeno-2,2'-biphenol (Patent Document 3), there is no description of a method for producing optical isomers.

On the other hand, optically active 2,2'-biphenol derivatives represented by the following formulas (B) and (C):

[CHEMICAL 2]

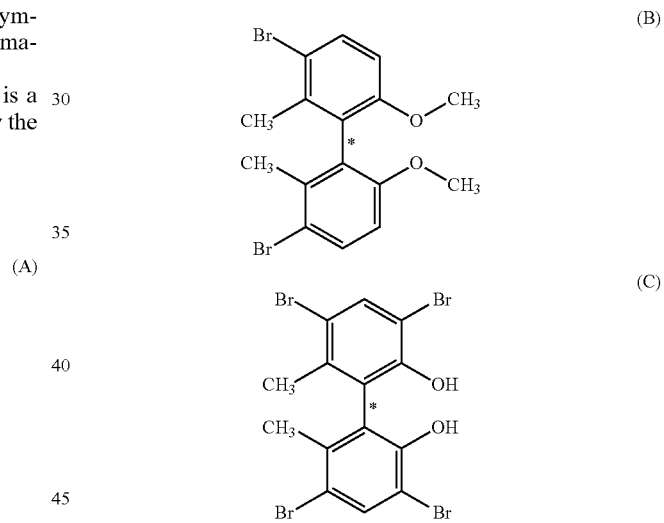

(wherein, * is the same as previously defined) are useful as precursors of asymmetric phase-transfer catalysts.

However, since both of these compounds are synthesized from optically active 6,6'-dimethyl-2,2'-biphenol represented by the aforementioned formula (A) (Non-Patent Document 2), they have the same problems as the previously described production methods.

[Patent Document 1] Japanese Unexamined Patent Application, First Publication No. 2004-189696

[Patent Document 2] Japanese Unexamined Patent Application, First Publication No. H10-45648

[Patent Document 3] Japanese Unexamined Patent Application Publication (Translation of PCT Application) No. 2005-510551

[Non-Patent Document 1] SYNLETT, 1995, No. 3, 283-284

[Non-Patent Document 2] Organic Process Research & Development, Vol. 11, pp 628-632, 2007

DISCLOSURE OF THE INVENTION

In consideration of the actual circumstances surrounding the prior art as described above, an object of the present invention is to provide a production method that enables simple and efficient production of an optically active 6,6'-disubstituted-2,2'-biphenol derivative.

As a result of conducting extensive research to solve the aforementioned problems, the inventors of the present invention found that:

(A) by allowing an optically active diamine compound to act on an optical isomer mixture of a 6,6'-disubstituted-5,5'-dihalogeno-3,3'-disubstituted-2,2'-biphenol derivative represented by the following formula (2'), only one optical isomer of the 6,6'-disubstituted-5,5'-dihalogeno-3,3'-disubstituted-2,2'-biphenol derivative forms a salt with the aforementioned optically active diamine compound, the salt can be isolated as a crystalline product, and an optically active 6,6'-disubstituted-5,5'-dihalogeno-3,3'-disubstituted-2,2'-biphenol derivative represented by the following formula (2) can be efficiently obtained from the isolated salt, and by further reacting with a Lewis acid, a 6,6'-disubstituted-2,2'-biphenol derivative represented by the following formula (3) can be efficiently obtained;

(B) by reacting the resulting optically active 6,6'-disubstituted-5,5'-dihalogeno-3,3'-disubstituted-2,2'-biphenol derivative represented by the following formula (2) with a Brønsted acid, an optically active 6,6'-disubstituted-5,5'-dihalogeno-2,2'-biphenol derivative represented by the following formula (1) can be efficiently obtained, and by further reacting with a Lewis acid, the 6,6'-disubstituted-2,2'-biphenol derivative represented by the following formula (3) can be efficiently obtained; and, (C) the 6,6'-disubstituted-5,5'-dihalogeno-3,3'-disubstituted-2,2'-biphenol derivative represented by the following formula (2') is efficiently obtained by reacting a 5-substituted-4-halogeno-2-substituted-phenol derivative represented by the following formula (4) with a copper salt and an organic base or cupric oxyhalide organic base complex, thereby leading to completion of the present invention.

Thus, according to a first aspect of the present invention, a method is provided for producing a 6,6'-disubstituted-2,2'-biphenol derivative represented by the following formula (3):

[CHEMICAL 3]

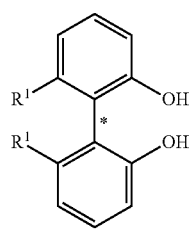

(3)

(wherein, $R^1$ represents an optionally substituted primary or secondary alkyl group having 1 to 10 carbon atoms or an optionally substituted cycloalkyl group having 3 to 10 carbon atoms, and * represents an axially asymmetric center), comprising: allowing an optically active diamine to act on a 6,6'-disubstituted-5,5'-dihalogeno-3,3'-disubstituted-2,2'-biphenol derivative represented by the following formula (2'):

[CHEMICAL 4]

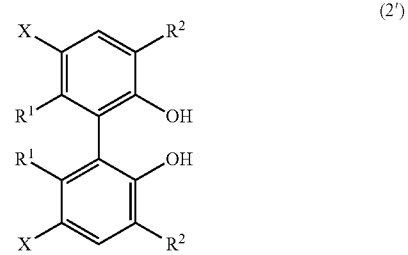

(2')

(wherein, $R^1$ is the same as previously defined, $R^2$ represents a tertiary alkyl group having 4 to 6 carbon atoms, and X represents a halogen atom), separating the resulting salt, and then neutralizing the salt to obtain an optically active 6,6'-disubstituted-5,5'-dihalogeno-3,3'-disubstituted-2,2'-biphenol derivative represented by the following formula (2):

[CHEMICAL 5]

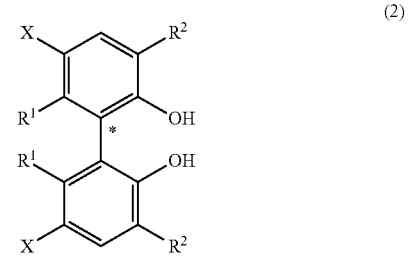

(2)

(wherein, $R^1$, $R^2$, X and * are the same as previously defined), followed by further allowing a Lewis acid to act on the compound represented by formula (2).

According to a second aspect of the present invention, a method is provided for producing the 6,6'-disubstituted-2,2'-biphenol derivative represented by the aforementioned formula (3), comprising: allowing an optically active diamine to act on the 6,6'-disubstituted-5,5'-dihalogeno-3,3'-disubstituted-2,2'-biphenol derivative represented by the aforementioned formula (2'), separating the resulting salt, and then neutralizing the salt to obtain the optically active 6,6'-disubstituted-5,5'-dihalogeno-3,3'-disubstituted-2,2'-biphenol derivative represented by the aforementioned formula (2), followed by allowing a Brønsted acid to act on the compound represented by the aforementioned formula (2) to obtain an optically active 6,6'-disubstituted-5,5'-dihalogeno-2,2'-biphenol derivative represented by the following formula (1):

[CHEMICAL 6]

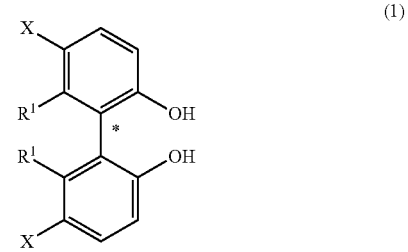

(1)

(wherein, $R^1$, X and * are the same as previously defined), and allowing a Lewis acid to act on the compound represented by formula (1).

According to a third aspect of the present invention, a method is provided for producing the 6,6'-disubstituted-5,5'-dihalogeno-3,3'-disubstituted-2,2'-biphenol derivative represented by the aforementioned formula (2), comprising: allowing an optically active diamine compound to act on an optical isomer mixture of the 6,6'-disubstituted-5,5'-dihalogeno-3,3'-disubstituted-2,2'-biphenol derivative represented by formula (2') to obtain a salt of one optical isomer of the 6,6'-disubstituted-5,5'-dihalogeno-3,3'-disubstituted-2,2'-biphenol derivative represented by formula (2') and the optically active diamine compound, followed by isolating the optically active 6,6'-disubstituted-5,5'-dihalogeno-3,3'-disubstituted-2,2'-biphenol derivative represented by the aforementioned formula (2) from this salt.

In the production method of the present invention, a 1,2-diaminoalkane derivative is preferably used as the optically active diamine compound.

According to a fourth aspect of the present invention, an optically active 6,6'-disubstituted-5,5'-dihalogeno-2,2'-biphenol derivative is provided that is represented by the aforementioned formula (1).

According to a fifth aspect of the present invention, an optically active 6,6'-disubstituted-5,5'-dihalogeno-3,3'-disubstituted-2,2'-biphenol derivative is provided that is represented by the aforementioned formula (2).

According to a sixth aspect of the present invention, a 6,6'-disubstituted-5,5'-dihalogeno-3,3'-disubstituted-2,2'-biphenol derivative is provided that is represented by the aforementioned formula (2').

According to a seventh aspect of the present invention, a method is provided for producing the 6,6'-disubstituted-5,5'-dihalogeno-2,2'-biphenol derivative represented by the aforementioned formula (2'), comprising: allowing a copper salt and an organic base or cupric oxyhalide organic base complex to act on a 5-substituted-4-halogeno-2-substituted-phenol derivative represented by the following formula (4):

[CHEMICAL 7]

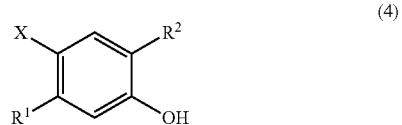

(4)

(wherein, $R^1$, $R^2$ and X are the same as previously defined).

According to an eighth aspect of the present invention, a method is provided for producing the optically active 6,6'-disubstituted-5,5'-dihalogeno-2,2'-biphenol derivative represented by the aforementioned formula (1), comprising: allowing a Brønsted acid to act on the optically active 6,6'-disubstituted-5,5'-dihalogeno-3,3'-disubstituted-2,2'-biphenol derivative represented by the aforementioned formula (2).

According to a ninth aspect of the present invention, a method is provided for producing the optically active 6,6'-disubstituted-2,2'-biphenol derivative represented by the aforementioned formula (3), comprising: allowing a Lewis acid to act on the optically active 6,6'-disubstituted-5,5'-dihalogeno-2,2'-biphenol derivative represented by the aforementioned formula (1).

According to the present invention, a novel, optically active 2,2'-biphenol derivative is provided that is highly valuable for use in fields relating to the production of pharmaceutical and agrichemical bulk drugs and their production intermediates.

In addition, according to the present invention, a 2,2'-biphenol derivative having high optical purity can be produced simply and efficiently.

BEST MODES FOR CARRYING OUT THE INVENTION

The following provides a detailed explanation of the present invention.
1) The present invention relates to a production method of an optically active 6,6'-disubstituted-2,2'-biphenol derivative represented by the aforementioned formula (3) (hereinafter also be referred to as "optically active biphenol derivative (3)").

The optically active biphenol derivative (3) can be obtained by allowing a Lewis acid to act on an optically active 6,6'-disubstituted-5,5'-dihalogeno-3,3'-disubstituted-2,2'-biphenol derivative represented by the aforementioned formula (2) (hereinafter also be referred to as "optically active biphenol derivative (2)").

The optically active biphenol derivative (2) can be obtained by allowing an optically active diamine compound to act on an optical isomer mixture of a 6,6'-disubstituted-5,5'-dihalogeno-3,3'-disubstituted-2,2'-biphenol derivative represented by the aforementioned formula (2') (hereinafter also be referred to as "biphenol derivative (2')") to obtain a salt of one optical isomer of the biphenol derivative (2') and the optically active diamine compound, and then neutralizing the salt.

(Optically Active Biphenol Derivative (2), Optically Active Biphenol Derivative (3) and Biphenol Derivative (2'))

In formulas (2), (3) and (2'), $R^1$ represents an optionally substituted primary or secondary alkyl group having 1 to 10 carbon atoms, or an optionally substituted cycloalkyl group having 3 to 10 carbon atoms.

Specific examples of primary or secondary alkyl groups having 1 to 10 carbon atoms for $R^1$ include a methyl group, ethyl group, n-propyl group, i-propyl group, n-butyl group, i-butyl group, s-butyl group, n-pentyl group, n-hexyl group, n-heptyl group, n-octyl group, n-nonyl group and n-decyl group.

Specific examples of cycloalkyl groups having 3 to 10 carbon atoms include a cyclopropyl group, cyclobutyl group, cyclopentyl group, cyclohexyl group and cyclooctyl group.

Examples of substitutents of the primary or secondary alkyl groups having 1 to 10 carbon atoms for $R^1$ include alkoxy groups having 1 to 10 carbon atoms such as a methoxy group, ethoxy group, propoxy group or isopropoxy group; optionally substituted phenyl groups such as a phenyl group, 4-methylphenyl group or 2-chlorophenyl group; and alkoxycarbonyl groups having 1 to 10 carbon atoms such as a methoxycarbonyl group, ethoxycarbonyl group, propoxycarbonyl group or isopropoxycarbonyl group.

Examples of substituents of the cycloalkyl groups having 3 to 10 carbon atoms include alkoxy groups having 1 to 10 carbon atoms such as a methoxy group, ethoxy group, propoxy group or isopropoxy group; optionally substituted phenyl groups such as a phenyl group, 4-methylphenyl group or 2-chlorophenyl group; and alkoxycarbonyl groups having 2 to 10 carbon atoms such as a methoxycarbonyl group, ethoxycarbonyl group, propoxycarbonyl group or isopropoxycarbonyl group.

In formulas (2), (3) and (2'), * represents an axially asymmetric center, or in other words, indicates that one axially asymmetric isomer is in excess with respect to the other axially asymmetric isomer in the structure of the biphenyl moiety of optically active biphenol derivative (3).

In formulas (2) and (2'), X represents a halogen atom such as a fluorine atom, chlorine atom, bromine atom or iodine atom.

In formulas (2) and (2'), $R^2$ represents a tertiary alkyl group having 4 to 6 carbon atoms. Specific examples of tertiary alkyl groups having 4 to 6 carbon atoms include a t-butyl group, 1,1-dimethylpropyl group and 1,1,2-trimethylpropyl group.

Specific examples of the optically active biphenol derivative (2) are shown in the following Table 1. The optically active biphenol derivative. (2) of the present invention is not limited thereto.

TABLE 1

(2)

[Structure: biphenol derivative with X, $R^2$, $R^1$, OH groups]

| $R^1$ | $R^2$ | X |
|---|---|---|
| $CH_3$ | t-$C_4H_9$ | Cl |
| $CH_3$ | t-$C_4H_9$ | Br |
| $CH_3$ | t-$C_4H_9$ | I |
| $CH_3$ | $C(CH_3)_2(C_2H_5)$ | Cl |
| $CH_3$ | $C(CH_3)_2(C_2H_5)$ | Br |
| $C_2H_5$ | t-$C_4H_9$ | Br |
| $C_2H_5$ | $C(CH_3)_2(C_2H_5)$ | Br |
| n-$C_3H_7$ | t-$C_4H_9$ | Br |
| i-$C_3H_7$ | t-$C_4H_9$ | Br |
| n-$C_4H_9$ | t-$C_4H_9$ | Br |
| c-Pr | t-$C_4H_9$ | Br |
| c-Pr | $C(CH_3)_2(C_2H_5)$ | Br |
| c-Pen | t-$C_4H_9$ | Br |
| c-Hex | t-$C_4H_9$ | Br |

(Optically Active Diamine Compound and Optical Resolution Treatment)

Although there are no particular limitations on the optically active diamine compound used in the present invention provided it is an optically active compound that has two amino groups in a molecule thereof, an optically active 1,2-diaminoalkane derivative is preferable since it is readily available and enables more efficient optical resolution.

Specific examples of 1,2-diaminoalkane derivatives include 1,2-diaminopropane, 1-phenyl-1,2-diaminoethane, 3-phenyl-1,2-diaminopropane, 2,3-butanediamine, 1,2-diphenyl-1,2-diaminoethane, 1,2-bis(1-naphthyl)-1,2-diaminoethane, 1,2-bis(2-naphthyl)-1,2-diaminoethane, 1,2-cyclohexanediamine, 2-(aminomethyl)pyrrolidine and 2,3-dimethylpyrazine, and examples of optically active 1,2-diaminoalkanes include optical isomers of these specific examples. Optically active 1,2-diphenyl-1,2-diaminoethane is particularly preferable.

The molar ratio of the biphenol derivative (2') and the optically active diamine compound used in the reaction for forming a salt composed of one optical isomer of the biphenol derivative (2') and the optically active diamine compound [biphenol derivative (2')]: (optically active diamine compound) is 0.3:1 to 1:2 and preferably 0.5:1 to 1:1.

The reaction for forming a salt from the biphenol derivative (2') and the optically active diamine compound by allowing the optically active diamine compound to act on the optical isomer mixture of the biphenol derivative (2') can be carried out in a suitable solvent.

A solvent can be used for the solvent used without any particular limitations provided it is inert with respect to the biphenol derivative (2') and the optically active diamine compound and does not demonstrate any significant interaction. In particular, a solvent is preferably selected so that, after having formed a salt from the biphenol derivative (2') and the optically active diamine compound, one diastereomer of the resulting diastereomer mixture is selectively precipitated from the reaction system as a crystalline product.

Preferable examples of solvents include alkane-based solvents such as pentane, hexane, heptane, Isopar E or Isopar G; aromatic-based solvents such as benzene, toluene or ortho-xylene; halogen-based solvents such as methylene chloride, chloroform, dichloroethane or chlorobenzene; ester-based solvents such as methyl acetate or ethyl acetate; ether-based solvents such as diethyl ether or tetrahydrofuran; and mixed solvents of two or more types thereof. In particular, toluene or a mixed solvent of toluene and an alkane-based solvent is preferable.

Although there are no particular limitations on the amount of solvent used, when represented as the ratio of [biphenol derivative (2') (parts by weight)]:[solvent (parts by volume)], this ratio is normally 1:1 to 1:100 and preferably 1:3 to 1:40.

Although there are no particular limitations on the method of the reaction for forming a salt from an optical isomer mixture of the biphenol derivative (2') and the optically active diamine compound, specific examples of that method are described in (a) to (c) below:

(a) a method in which prescribed amounts of a mixture of racemic forms of biphenol derivative (2') and optically active diamine compound are dissolved in a solvent while heating under the temperature less than or equal to the boiling point of the solvent, followed by allowing to stand or suitably stirring at room temperature or while cooling;

(b) a method in which a prescribed amounts of biphenol derivative (2') and optically active diamine compound are dissolved in a solvent while heating under the temperature less than or equal to the boiling point of the solvent, followed by adding a solvent having low solubility while stirring; and, (c) a method in which a prescribed amount of optically active diamine compound is added to biphenol derivative (2') while suspended in a suitable solvent, followed by stirring the total volume thereof.

This reaction forms a salt of only one of the two types of optical isomers of the biphenol derivative (2') and the optically active diamine compound. Which of the two types of optical isomers of the biphenol derivative (2') is preferentially used to form the salt depends on the optically active diamine compound used.

Since a salt of one optical isomer of the biphenol derivative (2') and the optically active diamine compound normally precipitates from the reaction system as a crystalline product, the salt of one optical isomer of the biphenol derivative (2') and the optically active diamine compound can be isolated by filtering the reaction liquid.

Next, the isolated salt of one optical isomer of the biphenol derivative (2') and the optically active diamine compound is stirred in a mixed solvent of a non-water-soluble organic solvent and an acidic aqueous solution followed by liquid separation. A desired optically active biphenol derivative (2) can be obtained at high optical purity by concentrating the resulting non-water-soluble organic solvent phase.

There are no particular limitations on the non-water-soluble organic solvent used, and examples include alkane-based solvents such as pentane, hexane, heptane, Isopar E or Isopar G; aromatic-based solvents such as benzene, toluene or ortho-xylene; halogen-based solvents such as methylene chloride, chloroform, dichloroethane or chlorobenzene; ester-based solvents such as methyl acetate or ethyl acetate; ether-based solvents such as diethyl ether or cyclopropyl methyl ether; and mixed solvents of two or more types thereof. In particular, aromatic-based solvents can be used preferably.

The ratio at which the crystalline product and the non-water-soluble organic solvent are used [crystalline product (parts by weight)]:[non-water-soluble solvent (parts by volume)] is normally 1:1 to 1:50 and preferably 1:3 to 1:10.

Although examples of acidic aqueous solutions that can be used include aqueous solutions of inorganic acids such as hydrogen chloride or sulfuric acid; and aqueous solutions of organic acids such as acetic acid, propionic acid or methanesulfonic acid, hydrochloric acid is preferable from a practical viewpoint.

There are no particular limitations on the acid concentration of the acidic aqueous solution, and although an acidic aqueous solution can be used having an acid concentration from 0.1 N to that of a saturated aqueous solution, an aqueous solution having an acid concentration of 0.5 to 5 N is preferable.

Although the amount of the acidic aqueous solution used depends on the acid concentration and the stoichiometric amount of the optically active diamine compound contained in the crystalline product, it is normally 1 to 20 times moles and preferably 2 to 10 times moles based on 1 mole of the optically active diamine compound.

The temperature during stirring and liquid separation of the crystalline product in the mixed solvent of the non-water-soluble organic solvent and acidic aqueous solution is such that the stirring and liquid separation can be suitably carried out from the melting point to the boiling point of the non-water-soluble organic solvent and acidic aqueous solution, the temperature is preferably from 0 to 50° C.

In addition, the other optical isomer of the biphenol derivative (2') is contained in the reaction liquid obtained after isolating the salt of one of the optical isomers of the biphenol derivative (2') and the optically active diamine compound from the reaction liquid of the mixture of optical isomers of the biphenol derivative (2') and the optically active diamine compound. This other optical isomer of the biphenol derivative (2') can be isolated from the reaction liquid by ordinary methods.

Moreover, the optically active diamine compound used in the reaction can also be recovered from the reaction liquid by ordinary methods and reused.

Although an optically active biphenol derivative (2) can be efficiently separated from the biphenol derivative (2') according to the above-mentioned method, this phenomenon is due to the presence of a halogen atom and tertiary alkyl group as substituents on the benzene ring of the compound. In addition, these substituents can be easily removed by treatment with Lewis acid as described below when necessary in terms of synthesizing the target ligand for asymmetric synthesis.

(Lewis Acid and Lewis Acid Treatment)

Examples of Lewis acids used include copper chloride, zinc chloride, aluminum chloride, titanium tetrachloride and zirconium chloride. One type of these Lewis acids can be used alone or two or more types can be used in combination.

The amount of Lewis acid used is 0.01 to 20 times moles and preferably 0.1 to 10 times moles based on 1 mole of the optically active biphenol derivative (2).

This reaction can be carried out in an inert solvent. Examples of solvents used include alkane-based solvents such as pentane, hexane, heptane, Isopar E or Isopar G; aromatic-based solvents such as benzene, toluene or ortho-xylene; halogen-based solvents such as methylene chloride, chloroform, dichloroethane or chlorobenzene; and mixed solvents composed of two or more types thereof.

In the case of using an alkane-based or halogen-based solvent, an aromatic-based solvent such as benzene, toluene or ortho-xylene is preferably suitably mixed therewith as an acceptor of the halogen atom eliminated from the optically active biphenol derivative (2).

Although there are no particular limitations on the amount of solvent used, the amount of solvent used when represented as the ratio of [optically active biphenol derivative (2) (parts by weight)]:[solvent (parts by volume)] is normally 1:3 to 1:100 and preferably 1:4 to 1:40.

Although the treatment temperature is such that treatment can be suitably carried out from the melting point to the boiling point of the solvent, the temperature is preferably from 0 to 50° C.

2) The present invention also results to a production method of an optically active biphenol derivative (3) by going through an optically active 6,6'-disubstituted-5,5'-dihalogeno-2,2'-biphenol derivative (hereinafter also be referred to as "optically active biphenol derivative (1)") represented by the aforementioned formula (1) (wherein, $R^1$ and X have the same meanings as indicated in the aforementioned formula (2)). The optically active biphenol derivative (1) is also useful as a synthetic intermediate of a ligand for asymmetric synthesis.

The optically active biphenol derivative (1) can be obtained by allowing a Brønsted acid to act on the optically active biphenol derivative (2) obtained by optical resolution treatment. Moreover, the optically active biphenol derivative (3) can be obtained by allowing a Lewis acid to act on the optically active biphenol derivative (1).

(Optically Active Biphenol Derivative (1))

Specific examples of the optically active biphenol derivative (1) are shown in the following Table 2. The optically active biphenol derivative (1) of the present invention is not limited thereto. In Table 1, c-Pr represents a cyclopropyl group, c-Pen a cyclopentyl group, and c-Hex a cyclohexyl group (and to apply similarly hereinafter).

TABLE 2

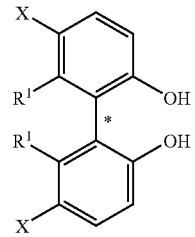

(1)

| $R^1$ | X |
|---|---|
| $CH_3$ | Cl |
| $CH_3$ | Br |
| $CH_3$ | I |
| $CH_3$ | Cl |
| $CH_3$ | Br |

TABLE 2-continued

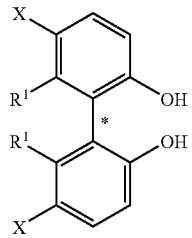

(1)

| R¹ | X |
|---|---|
| C₂H₅ | Br |
| C₂H₅ | Br |
| n-C₃H₇ | Br |
| i-C₃H₇ | Br |
| n-C₄H₉ | Br |
| c-Pr | Br |
| c-Pr | Br |
| c-Pen | Br |
| c-Hex | Br |

(Brønsted Acid and Brønsted Acid Treatment)

Examples of Brønsted acids used in the present invention include inorganic acids such as hydrochloric acid or sulfuric acid; organic sulfonic acids such as para-toluenesulfonic acid or methanesulfonic acid; fluoroalkanic acids such as trifluoroacetic acid or perfluoropropionic acid; fluoroalkanesulfonic acids such as trifluoromethanesulfonic acid or perfluorobutanesulfonic acid; and polymeric sulfonic acids. One type of these Brønsted acids can be used alone or two or more types can be used in combination.

Among these Brønsted acids, fluoroalkanesulfonic acids such as trifluoromethanesulfonic acid or perfluorobutanesulfonic acid are preferable.

The molar ratio at which the optically active biphenol derivative (2) and the Brønsted acid are used [optically active biphenol derivative (2)]:(Brønsted acid) is normally 10:1 to 1:10 and preferably 10:2 to 1:4.

The reaction between the optically active biphenol derivative (2) and the Brønsted acid can be carried out in a suitable solvent. Examples of solvents used include alkane-based solvents such as pentane, hexane, heptane, Isopar E or Isopar G; aromatic-based solvents such as benzene, toluene or ortho-xylene; halogen-based solvents such as methylene chloride, chloroform, dichloroethane or chlorobenzene; and mixed solvents of two or more types thereof.

In the case of using an alkane-based or halogen-based solvent, an aromatic-based solvent such as benzene, toluene or ortho-xylene is preferably suitably mixed therewith as an acceptor of the alkyl group eliminated from the optically active phenol derivative (2).

Although there are no particular limitations on the amount of solvent used, when represented as the ratio of [optically active biphenol derivative (2) (parts by weight)]:[Brønsted acid aqueous solution (parts by volume)], this ratio is normally 1:3 to 1:100 and preferably 1:5 to 1:50.

Although the treatment temperature is such that treatment can be suitably carried out from the melting point to the boiling point of the solvent, the temperature is preferably from 0 to 50° C.

(Lewis Acid and Lewis Acid Treatment)

Examples of Lewis acids used include copper chloride, zinc chloride, aluminum chloride, titanium tetrachloride and zirconium chloride. One type of these Lewis acids can be used alone or two or more types can be used in combination.

The amount of Lewis acid used is 0.01 to 20 times moles and preferably 0.1 to 10 times moles based on 1 mole of the optically active biphenol derivative (1).

This reaction can be carried out in an inert solvent. Examples of solvents used include alkane-based solvents such as pentane, hexane, heptane, Isopar E or Isopar G; aromatic-based solvents such as benzene, toluene or ortho-xylene; halogen-based solvents such as methylene chloride, chloroform, dichloroethane or chlorobenzene; and mixed solvents of two or more types thereof.

In the case of using an alkane-based or halogen-based solvent, an aromatic-based solvent such as benzene, toluene or ortho-xylene is preferably suitably mixed therewith as an acceptor of the halogen atom eliminated from the optically active biphenol derivative (1).

Although there are no particular limitations on the amount of solvent used, when represented as the ratio of [optically active biphenol derivative (1) (parts by weight)]:[solvent (parts by volume)], this ratio is normally 1:3 to 1:100 and preferably 1:4 to 1:40.

Although the treatment temperature is such that treatment can be suitably carried out from the melting point to the boiling point of the solvent, the temperature is preferably from 0 to 50° C.

3) The present invention also relates to a production method of the biphenol derivative (2').

The biphenol derivative (2') can be obtained by allowing a copper salt and an organic base or cupric oxyhalide organic base complex to act on a 5-substituted-4-halogeno-2-substituted-phenol derivative (hereinafter also be referred to as "phenol derivative (4)") represented by the aforementioned formula (4) (wherein, $R^1$, $R^2$ and X have the same meanings as indicated in the aforementioned formula (2')).

(Copper Salt and Organic Base)

Examples of copper salts used include cuprous chloride, cuprous bromide and cuprous iodide, while examples of organic bases include tetramethylethylenediamine, dimethylethylenediamine, ethylenediamine, DABCO, DBU, triethylamine, diisopropylethylamine, dimethylamine, diethylamine, dibutylamine, diisopropylamine, pyrrolidine, ammonia, methylamine, ethylamine, butylamine, isopropylamine, benzylamine, t-butylamine, pyridine, 2,6-lutidine, DMAP, pyrimidine, aniline, N-methylaniline, N,N-dimethylaniline, N-methylmorpholine, diphenylethylenediamine, phenethylamine, cyclohexanediamine, sparteine and cinchonine. In particular, tetramethylethylenediamine, dibutylamine, t-butylamine and phenethylamine are preferable.

One type of these copper salts can be used alone or two or more types can be used in combination. In addition, one type of organic base can be used alone or two or more types can be used in combination. Reactions using these copper salts and organic bases can be carried out in the presence of oxygen or oxidizing agent. Examples of methods carried out in the presence of oxygen include methods carried out in oxygen or air.

The amount of copper salt used is 0.01 to 20 times moles and preferably 0.1 to 10 times moles based on 1 mole of the phenol derivative (4).

The amount of organic base used is 0.5 to 5 times moles and preferably 1.0 to 3.0 times moles based on 1 mole of copper salt.

(Cupric Oxyhalide Organic Base Complex)

In addition, a cupric oxyhalide organic base complex can also be used that has been prepared in advance from the aforementioned copper salt and organic base.

The amount of cupric oxyhalide organic base complex used is 0.01 to 20 times moles and preferably 0.1 to 10 times moles based on 1 mole of the phenol derivative (4).

Although there are no particular limitations on the solvent used in this reaction provided it does not inhibit the reaction, examples of solvents that can be used include hydrocarbon-based solvents such as hexane, cyclohexane, benzene or toluene; chlorine-based solvents such as methylene chloride, chloroform, carbon tetrachloride or chlorobenzene; nitrile-based solvents such as acetonitrile or benzonitrile; ketone-based solvents such as acetone, ethyl methyl ketone or tert-butyl methyl ketone; amide-based solvents such as DMF, N-methylpyrrolidin-2-one (NMP) or N,N'-dimethylimidazolidin-2-one (DMI); and DMSO.

In addition, the reaction can be carried out in a 2-solution two-phase system of water and organic solvent. In the case of carrying out the reaction in a 2-solution two-phase system, a non-water-soluble solvent in the manner of hydrocarbon-based solvents such as hexane, cyclohexane, benzene or toluene, or a chlorine-based solvents such as methylene chloride, chloroform or chlorobenzene, is preferably used alone or as a mixture, and hydrocarbon-based solvents such as hexane, cyclohexane, benzene or toluene can be used more preferably alone or as a mixture.

Although there are no particular limitations on the amount of solvent used, when represented as the ratio of [phenol derivative (4) (parts by weight)]:[solvent (parts by volume)], this ratio is normally 1:3 to 1:100 and preferably 1:4 to 1:40.

Although the treatment temperature is such that treatment can be suitably carried out from the melting point to the boiling point of the solvent, the temperature is preferably from 0 to 50° C.

In any of the reactions, the target compound can be efficiently isolated by carrying out a post-treatment procedure ordinarily used in organic synthesis chemistry, and as necessary, conventionally known separation and purification means, following completion of the reaction.

The structure of a target compound can be identified and confirmed by measurement of $^1$H-NMR spectrum, IR spectrum or mass spectrum, or by elementary analysis and the like.

EXAMPLES

Although the following provides a detailed explanation of the present invention through examples and reference examples, the present invention is not limited thereto.

The optical purity of reaction products was determined using an optical resolution column.

Measurement conditions of the optical resolution column are indicated below.

HPLC column: Chiralcel OG (0.46 cm$\phi$×25 cm, Daicel Chemical Industries, Ltd.)
Carrier: n-hexane/ethanol=97/3 (1 ml/min)
Detection wavelength: 254 nm
Column temperature: 30° C.
Retention time: 12 min Example 1

Optical Resolution of Racemic Form of 6,6'-Dimethyl-5,5'-Dibromo-3,3'-Di(t-butyl)-2,2'-Biphenol

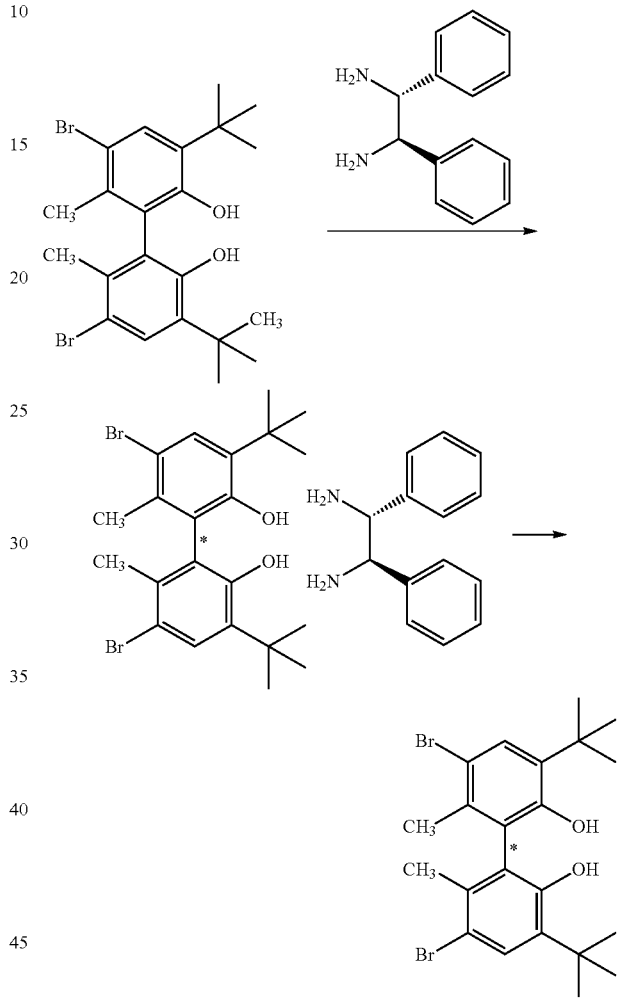

[CHEMICAL 8]

A racemic form of 6,6'-dimethyl-5,5'-dibromo-3,3'-di(t-butyl)-2,2'-biphenol (2.42 g, 5.00 mmol), (1R,2R)-1,2-diphenyl-1,2-diaminoethane (0.80 g, 3.75 mmol), toluene (5 ml) and hexane (25 ml) were mixed, and the entire volume was stirred for 1 hour at 70° C. followed by cooling to 5° C. and continuing to stir for 1 hour. The precipitated crystalline product was separated by filtering with a suction filter and the crystalline product remaining in the filter was washed with a mixed solvent of toluene and n-hexane (toluene:n-hexane=1:5 (v/v)) at 0° C. followed by drying under reduced pressure.

The crystalline product was a single diastereomer (1.57 g, yield 90.2% as 1:1 mixture of one of the enantiomers of 6,6'-dimethyl-5,5'-dibromo-3,3'-di(t-butyl)-2,2'-biphenol and (1R,2R)-1,2-diphenyl-1,2-diaminoethane).

$^1$H-NMR (CDCl$_3$) δ ppm: 7.5 (s, 2H), 7.3-7.1 (m, 10H), 4.1 (s, 2H), 2.0 (s, 6H), 1.4 (s, 18H)

The crystalline product obtained in the above procedure (1.57 g, converted no. of moles: 2.26 mmol), toluene (25 ml) and 2 N hydrochloric acid (40 ml) were mixed and stirred at room temperature for 1 hour followed by liquid separation. After washing the organic phase with water and drying with magnesium sulfate, the crystalline product was dried under reduced pressure to a solid to obtain 1.06 g of optically active 6,6'-dimethyl-5,5'-dibromo-3,3'-di(t-butyl)-2,2'-biphenol (converted yield: 88%, optical purity: >99% ee).

$^1$H-NMR (CDCl$_3$) δ ppm: 7.5 (s, 2H), 4.9 (s, 2H), 2.0 (s, 6H), 1.4 (s, 18H)

Example 2

Synthesis of Optically Active 6,6'-Dimethyl-5,5'-Dibromo-2,2'-Biphenol

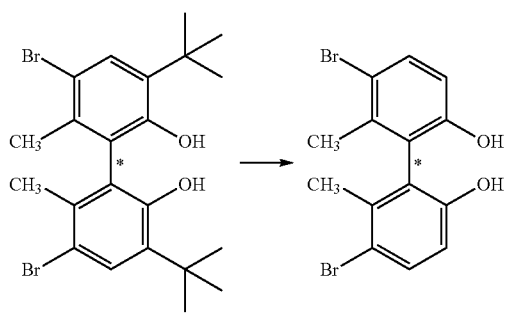

[CHEMICAL 9]

The optically active 6,6'-dimethyl-5,5'-dibromo-3,3'-di(t-butyl)-2,2'-biphenol obtained in Example 1 (1.06 g, optical purity: >99% ee, 2.2 mmol), toluene (5 ml) and trifluoromethanesulfonic acid (750 mg, 5 mmol) were mixed followed by stirring the entire volume for 1 hour at 5° C. Water (10 ml) and chloroform (20 ml) were then added to the reaction mixture followed by extraction and liquid separation. The organic phase was then washed with water and dried with anhydrous magnesium sulfate followed by distilling off the solvent under reduced pressure. N-hexane (10 ml) was added to the remaining slurry followed by stirring at room temperature, washing and filtering to obtain optically active 6,6'-dimethyl-5,5'-dibromo-2,2'-biphenol (761 mg, yield: 93%, optical purity: >99% ee).

$^1$H-NMR (CDCl$_3$) δ ppm: 7.6 (d, 2H, J=9.00), 6.8 (d, 2H, J=9.00), 4.6 (s, 2H), 2.1 (s, 6H)

Example 3

Synthesis of Optically Active 6,6'-Dimethyl-2,2'-Biphenol

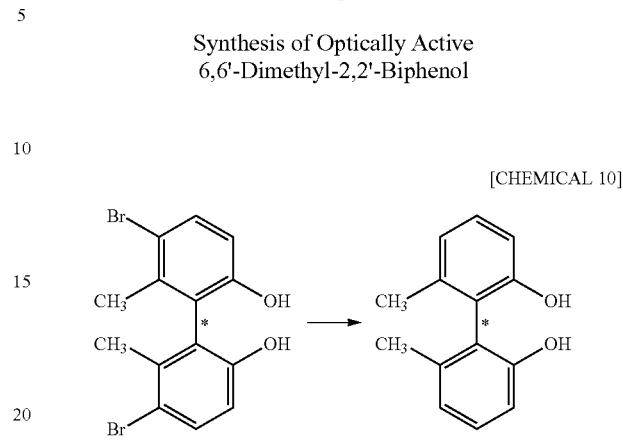

[CHEMICAL 10]

The optically active 6,6'-dimethyl-5,5'-dibromo-2,2'-biphenol obtained in Example 2 (372 mg, optical purity: >99% ee, 1.0 mmol), toluene (5 ml) and aluminum chloride (400 mg, 3.0 mmol) were mixed and the entire volume was stirred for 3 hours at 40° C. The reaction mixture was placed in ice-cooled dilute hydrochloric acid (1 N, 20 ml) followed by the addition of chloroform (30 ml), extraction and liquid separation. After washing the organic phase with water and drying with anhydrous magnesium sulfate, the solvent was distilled off under reduced pressure. N-hexane (10 ml) was added to the remaining slurry followed by stirring at room temperature, washing and filtering to obtain (S)-6,6'-dimethyl-2,2'-biphenol (197 mg, yield: 92%, optical purity: 99% ee)

Example 4

Production of Racemic Form of 6,6'-Dimethyl-5,5'-Dibromo-3,3'-Di(t-butyl)-2,2'-Biphenol

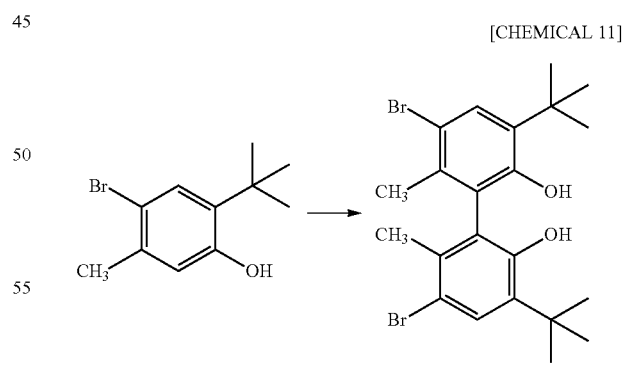

[CHEMICAL 11]

4-bromo-2-t-butyl-5-methylphenol (97.3 g, 0.4 mol), cupric oxychloride-tetramethylethylenediamine complex (4.6 g, 5 mol %) and sodium dodecyl sulfate (17.3 g, 15 mol %) were suspended in water (400 ml) and vigorously stirred for 9 hours at 90° C. in an oxygen atmosphere. Next, cupric oxychloride-tetramethylethylenediamine complex (2.2 g, 2.3 mol %) was further added followed by stirring for an additional 2 hours. After cooling the reaction mixture to room temperature, ethyl acetoacetate (300 ml) and concentrated hydrochloric acid (10 ml) were added followed by extraction and liquid separation to fractionate the organic phase. The aqueous phase was re-extracted with ethyl acetoacetate (200 ml). The organic phases were combined and after washing with water (300 ml×2), the combined organic phases were dried with anhydrous magnesium sulfate, concentrated and dried to a solid to obtain a crude product (98 g). The crude product was dispersed in n-hexane (200 ml) at room temperature and stirred for 1 hour followed by filtering and drying to obtain the target compound (37 g, yield: 35%).

Example 5

Production of Racemic Form of 6,6'-Dimethyl-5,5'-Dibromo-3,3'-Di(t-butyl)-2,2'-Biphenol 4-bromo-2-t-butyl-5-methylphenol (243 mg, 1.0 mmol), copper chloride (9.9 mg, 10 mol %) and phenethylamine (24 mg, 10 mol %) were dissolved in methylene chloride (2 ml) and vigorously stirred for 20 hours at 20° C. in air. Following completion of the reaction, ethyl acetate, water and an internal standard in the form of gallic aldehyde (19.6 mg, 0.1 mmol) were added. The organic phase was fractionated by extraction and liquid separation and then dried with anhydrous magnesium sulfate. $^1$H-NMR analysis was carried out on the crude product following concentration and drying to a solid to determine the yield (61%).

Example 6

Optical Resolution of Racemic Form of 6,6'-Dimethyl-5,5'-Dichloro-3,3'-Di(t-butyl)-2,2'-Biphenol A racemic form of 6,6'-dimethyl-5,5'-dichloro-3,3'-di(t-butyl)-2,2'-biphenol (273 mg, 0.7 mmol), (1R,2R)-1,2-diphenyl-1,2-diaminoethane (110 mg, 0.52 mmol), toluene (0.7 ml) and hexane (3.5 ml) were mixed, and the entire volume was stirred for 0.5 hours at 70° C. followed by cooling to 5° C. and continuing to stir for 1 hour. The precipitated crystalline product was separated by filtering with a suction filter and the crystalline product remaining in the filter was washed with a mixed solvent of toluene and n-hexane (toluene:n-hexane=1:5 (v/v)) at 0° C. followed by drying under reduced pressure.

The crystalline product was a single diastereomer (180 mg, yield 86% as 1:1 mixture of one of the enantiomers of 6,6'-dimethyl-5,5'-dichloro-3,3'-di(t-butyl)-2,2'-biphenol and (1R,2R)-1,2-diphenyl-1,2-diaminoethane).

The crystalline product obtained in the above procedure (180 mg, converted no. of moles: 0.29 mmol), toluene and 2 N hydrochloric acid were mixed and stirred at room temperature for 0.5 hours followed by liquid separation. After washing the organic phase with water and drying with magnesium sulfate, the crystalline product was dried under reduced pressure to a solid to obtain 110 mg of optically active 6,6'-dimethyl-5,5'-dichloro-3,3'-di(t-butyl)-2,2'-biphenol (converted yield: 93%).

$^1$H-NMR (CDCl$_3$) δ ppm: 7.38 (2H, s, ArH), 4.88 (2H, s, OH), 1.96 (6H, s, CH3), 1.40 (18H, s, tBu)

Example 7

Synthesis of Optically Active 6,6'-Dimethyl-5,5'-Dichloro-2,2'-Biphenol

The optically active 6,6'-dimethyl-5,5'-dichloro-3,3'-di(t-butyl)-2,2'-biphenol obtained in Example 6 (110 mg, optical purity: >99% ee, 0.28 mmol), toluene (5 ml) and trifluoromethanesulfonic acid (45 mg, 0.5 mmol) were mixed followed by stirring the entire volume for 1 hour at 5° C. Water (1 ml) and chloroform were then added to the reaction mixture followed by extraction and liquid separation. The organic phase was then washed with water and dried with anhydrous magnesium sulfate followed by distilling off the solvent under reduced pressure. N-hexane (10 ml) was added to the remaining slurry followed by stirring at room temperature, washing and filtering to obtain optically active 6,6'-dimethyl-5,5'-dichloro-2,2'-biphenol (70 mg, yield: 82%, optical purity: >99% ee).

$^1$H-NMR (CDCl$_3$) δ ppm: 7.37 (2H, d, J=8.7 Hz, ArH), 6.88 (2H, d, J=8.7 Hz, ArH), 4.63 (1H, s, OH), 2.04 (3H, s, CH3); $[a]_D^{24}$=−88.5° (c 1.00, MeOH)

Example 8

Production of Racemic Form of 6,6'-Dimethyl-5,5'-Dichloro-3,3'-Di(t-butyl)-2,2'-Biphenol 4-chloro-2-t-butyl-5-methylphenol (2.7 g, 13.6 mmol) and cupric oxychloride-tetramethylethylenediamine complex (0.16 g, 5 mol %) were dissolved in methylene chloride (10 ml) and vigorously stirred for 19 hours at 20° C. in air. Following completion of the reaction, ethyl acetoacetate and dilute hydrochloric acid were added followed by extraction, liquid separation and fractionation of the organic phase. After washing with water, the organic phase was dried with anhydrous magnesium sulfate, concentrated and dried to a solid to obtain a crude product. The crude product was re-crystallized using n-hexane to obtain the target compound (1.05 g, yield: 39%).

The invention claimed is:

1. A method for producing a 6,6'-disubstituted-2,2'-biphenol derivative represented by the following formula (3):

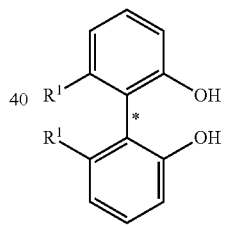

(3)

wherein, $R^1$ represents an optionally substituted primary or secondary alkyl group having 1 to 10 carbon atoms or an optionally substituted cycloalkyl group having 3 to 10 carbon atoms, and * represents an axially asymmetric center, comprising:

allowing an optically active diamine to act on a 6,6'-disubstituted-5,5'-dihalogeno-3,3'-disubstituted-2,2'-biphenol derivative represented by the following formula (2'):

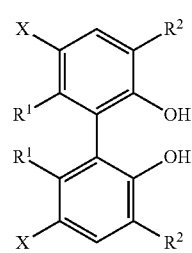

(2')

wherein, R¹ is the same as previously defined, R² represents a tertiary alkyl group having 4 to 6 carbon atoms, and X represents a halogen atom, separating the resulting salt, and then neutralizing the salt to obtain an optically active 6,6'-disubstituted-5,5'-dihalogeno-3,3'-disubstituted-2,2'-biphenol derivative represented by the following formula (2):

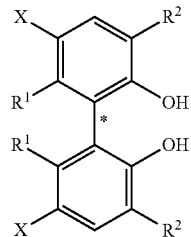

(2)

wherein, R¹, R², X and * are the same as previously defined, followed by further allowing a Lewis acid to act on the compound represented by formula (2).

2. A method for producing a 6,6'-disubstituted-2,2'-biphenol derivative represented by the following formula (3):

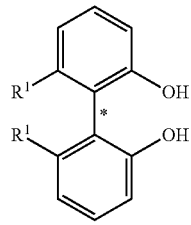

(3)

wherein, R¹ represents an optionally substituted primary or secondary alkyl group having 1 to 10 carbon atoms or an optionally substituted cycloalkyl group having 3 to 10 carbon atoms, and * represents an axially asymmetric center, comprising:

allowing an optically active diamine to act on a 6,6'-disubstituted-5,5'-dihalogeno-3,3'-disubstituted-2,2'-biphenol derivative represented by the following formula (2'):

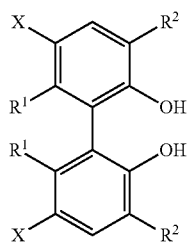

(2')

wherein, R¹ is the same as previously defined, R² represents a tertiary alkyl group having 4 to 6 carbon atoms, and X represents a halogen atom, separating the resulting salt, and then neutralizing the salt to obtain an optically active 6,6'-disubstituted-5,5'-dihalogeno-3,3'-disubstituted-2,2'-biphenol derivative represented by the following formula (2):

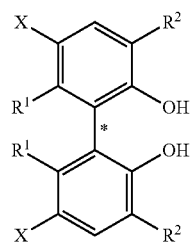

(2)

wherein, R¹, R², X and * are the same as previously defined, followed by allowing a Brønsted acid to act on the compound represented by formula (2) to obtain an optically active 6,6'-disubstituted-5,5'-dihalogeno-2,2'-biphenol derivative represented by the following formula (1):

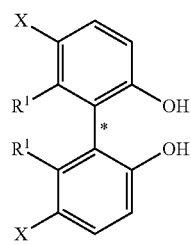

(1)

wherein, R¹, X and * are the same as previously defined, and allowing a Lewis acid to act on the compound represented by formula (1).

3. A method for producing an optically active 6,6'-disubstituted-5,5'-dihalogeno-3,3'-disubstituted-2,2'-biphenol derivative represented by the following formula (2):

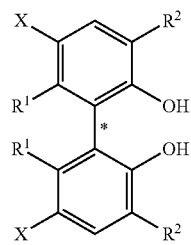

(2)

wherein, R¹ represents an optionally substituted primary or secondary alkyl group having 1 to 10 carbon atoms or an optionally substituted cycloalkyl group having 3 to 10 carbon atoms, R² represents a tertiary alkyl group having 4 to 6 carbon atoms, X represents a halogen atom, and * represents an axially asymmetric center, comprising:

allowing an optically active diamine compound to act on a 6,6'-disubstituted-5,5'-dihalogeno-3,3'-disubstituted-2,2'-biphenol derivative represented by the following formula (2'):

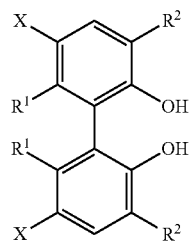

(2')

wherein, $R^1$, $R^2$ and X are the same as previously defined, separating the resulting salt, and then neutralizing the salt.

4. The method for producing according to claim 1, wherein the optically active diamine compound is a 1,2-diaminoalkane derivative.

5. An optically active 2,2'-biphenol derivative represented by the following formula (1):

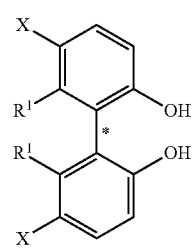

(1)

wherein, $R^1$ represents an optionally substituted primary or secondary alkyl group having 1 to 10 carbon atoms or an optionally substituted cycloalkyl group having 3 to 10 carbon atoms, X represents a halogen atom, and * represents an axially asymmetric center.

6. An optically active 2,2'-biphenol derivative represented by the following formula (2):

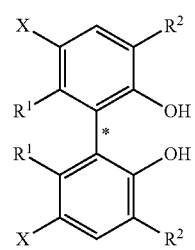

(2)

wherein, $R^1$ represents an optionally substituted primary or secondary alkyl group having 1 to 10 carbon atoms or an optionally substituted cycloalkyl group having 3 to 10 carbon atoms, $R^2$ represents a tertiary alkyl group having 4 to 6 carbon atoms, X represents a halogen atom, and * represents an axially asymmetric center.

7. A 2,2'-biphenol derivative represented by the following formula (2'):

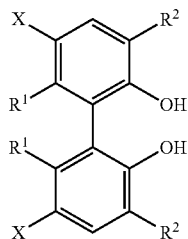

(2')

wherein, $R^1$ represents an optionally substituted primary or secondary alkyl group having 1 to 10 carbon atoms or an optionally substituted cycloalkyl group having 3 to 10 carbon atoms, $R^2$ represents a tertiary alkyl group having 4 to 6 carbon atoms, and X represents a halogen atom.

8. A method for producing a 6,6'-disubstituted-5,5'-dihalogeno-2,2'-biphenol derivative represented by following formula (2'):

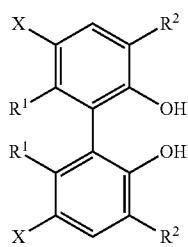

(2')

wherein, $R^1$ represents an optionally substituted primary or secondary alkyl group having 1 to 10 carbon atoms or an optionally substituted cycloalkyl group having 3 to 10 carbon atoms, $R^2$ represents a tertiary alkyl group having 4 to 6 carbon atoms, and X represents a halogen atom, comprising:

allowing a copper salt and an organic base or cupric oxyhalide organic base complex to act on a 5-substituted-4-halogeno-2-substituted-phenol derivative represented by the following formula (4):

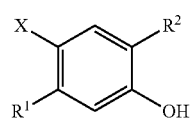

(4)

wherein, $R^1$, $R^2$ and X are the same as previously defined.

9. A method for producing an optically active 6,6'-disubstituted-5,5'-dihalogeno-2,2'-biphenol derivative represented by the following formula (1):

[CHEMICAL 15]

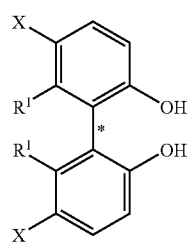
(1)

wherein, $R^1$ represents an optionally substituted primary or secondary alkyl group having 1 to 10 carbon atoms or an optionally substituted cycloalkyl group having 3 to 10 carbon atoms, X represents a halogen atom, and * represents an axially asymmetric center, comprising:
allowing a Brønsted acid to act on an optically active 6,6'-disubstituted-5,5'-dihalogeno-3,3'-disubstituted-2,2'-biphenol derivative represented by the following formula (2):

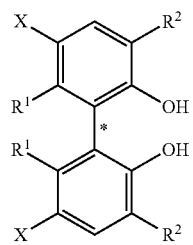
(2)

wherein, $R^1$, X and * are the same as previously defined, and $R^2$ represents a tertiary alkyl group having 4 to 6 carbon atoms.

10. A method for producing an optically active 6,6'-disubstituted-2,2'-biphenol derivative represented by the following formula (3):

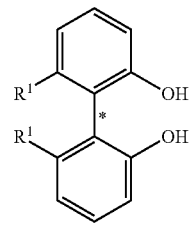
(3)

wherein, $R^1$ represents an optionally substituted primary or secondary alkyl group having 1 to 10 carbon atoms or an optionally substituted cycloalkyl group having 3 to 10 carbon atoms, and * represents an axially asymmetric center, comprising:
allowing a Lewis acid to act on an optically active 6,6'-disubstituted-5,5'-dihalogeno-2,2'-biphenol derivative represented by the following formula (1):

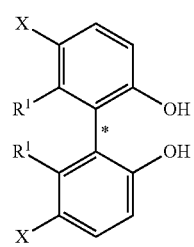
(1)

wherein, $R^1$ and * are the same as previously defined, and X represents a halogen atom.

11. The method for producing according to claim 2, wherein the optically active diamine compound is a 1,2-diaminoalkane derivative.

12. The method for producing according to claim 3, wherein the optically active diamine compound is a 1,2-diaminoalkane derivative.

* * * * *